(12) United States Patent
Xiao

(10) Patent No.: US 9,150,481 B2
(45) Date of Patent: Oct. 6, 2015

(54) PROCESS FOR PREPARING CYCLOHEXANOL AND CYCLOHEXANONE BY CYCLOHEXANE OXIDATION

(76) Inventor: Zaosheng Xiao, Suzhou (JP)

( * ) Notice: Subject to any disclaimer, the term of this patent is extended or adjusted under 35 U.S.C. 154(b) by 0 days.

(21) Appl. No.: 14/381,206

(22) PCT Filed: May 17, 2012

(86) PCT No.: PCT/CN2012/075632
§ 371 (c)(1),
(2), (4) Date: Aug. 26, 2014

(87) PCT Pub. No.: WO2013/143211
PCT Pub. Date: Oct. 3, 2013

(65) Prior Publication Data
US 2015/0073179 A1    Mar. 12, 2015

(30) Foreign Application Priority Data
Mar. 31, 2012    (CN) .......................... 2012 1 0091366

(51) Int. Cl.
*C07C 45/43*    (2006.01)
*C07C 29/50*    (2006.01)
*C07C 45/53*    (2006.01)
*C07C 29/132*    (2006.01)
*C07C 407/00*    (2006.01)
*C07C 29/159*    (2006.01)

(52) U.S. Cl.
CPC .............. *C07C 45/53* (2013.01); *C07C 29/132* (2013.01); *C07C 29/159* (2013.01); *C07C 407/00* (2013.01); *C07C 2101/14* (2013.01)

(58) Field of Classification Search
CPC ................................. C07C 45/43; C07C 29/50
USPC ......................................... 568/354, 357, 836
See application file for complete search history.

(56) References Cited

U.S. PATENT DOCUMENTS

2004/0158103 A1    8/2004   Pirutko et al.

FOREIGN PATENT DOCUMENTS

| CN | 1105970   A | 8/1995 |
|----|-------------|--------|
| CN | 1253938   A | 5/2000 |
| CN | 1621398   A | 6/2005 |
| CN | 1673320   A | 9/2005 |
| CN | 101172931 A | 5/2008 |

*Primary Examiner* — Sikarl Witherspoon

(57) ABSTRACT

A process for preparing cyclohexanol and cyclohexanone by cyclohexane oxidation, includes steps of: firstly processing uncatalyzed oxidation on cyclohexane by molecular oxygen, in such a manner that an oxidized mixture with cyclohexyl hydrogen peroxide serving as a primary product is generated; then decomposing the cyclohexyl hydrogen peroxide to produce cyclohexanol and cyclohexanone; and then distilling to obtain a cyclohexanol product and a cyclohexanone product, wherein the step decomposing the cyclohexyl hydrogen peroxide utilizes a three-step decomposition process including steps of: (1) performing the homogeneous catalytic decomposition by utilizing the bis(tert-butyl)chromate as a catalyst; (2) performing the heterogeneous catalytic decomposition of the sodium hydroxide alkaline aqueous solution under low alkalinity; and (3) performing the heterogeneous catalytic decomposition of the sodium hydroxide alkaline aqueous solution under high alkalinity.

18 Claims, 1 Drawing Sheet

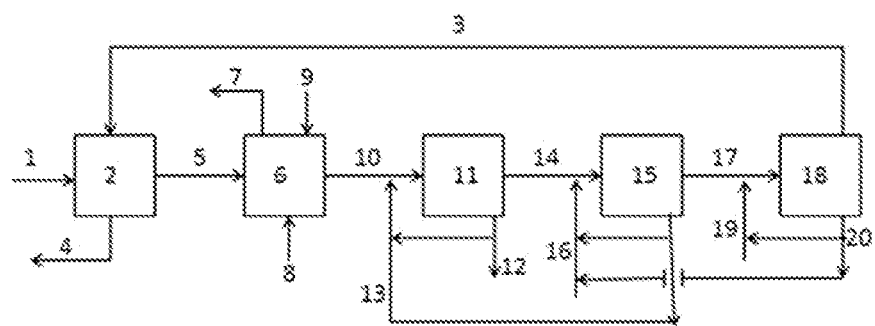

PROCESS FOR PREPARING CYCLOHEXANOL AND CYCLOHEXANONE BY CYCLOHEXANE OXIDATION

CROSS REFERENCE OF RELATED APPLICATION

This is a U.S. National Stage under 35 U.S.C 371 of the International Application PCT/CN2012/075632, filed May 17, 2012, which claims priority under 35 U.S.C. 119(a-d) to CN 201210091366.5, filed Mar. 31, 2012.

BACKGROUND OF THE PRESENT INVENTION

1. Field of Invention

The present invention relates to a process for preparing cyclohexanol and cyclohexanone by cyclohexane oxidation, and more particularly to a process for preparing cyclohexanol and cyclohexanone by cyclohexane oxidation comprising a three-step decomposition process for decomposing the cyclohexyl hydrogen peroxide.

2. Description of Related Arts

The conventional process for the preparation of cyclohexanol and cyclohexanone comprises: non-catalyticly oxidizing cyclohexane with molecular oxygen to obtain an oxidized mixture containing cyclohexyl hydroperoxide (CHHP) as a main product; decomposing the CHHP to obtain cyclohexanol and cyclohexanone; and rectifying to obtain products of the cyclohexanol and the cyclohexanone. Internationally, the art of decomposing the CHHP to obtain the cyclohexanol and the cyclohexanone comprises two manners: the homogeneous catalytic decomposition by bis(tert-butyl) chromate, disclosed by French Rhodia Company; and, the non-homogeneous catalytic decomposition by cobalt acetate in the alkaline aqueous solution of sodium hydroxide, disclosed by Dutch DSM. Both of the two manners are improved low-temperature decomposition techniques based on the conventional homogeneous catalytic oxidation process and the conventional saponification decomposition process by sodium hydroxide aqueous solution developed in the 1950s to 1970s.

Though having a molar yield up to 94% in the decomposition process, the homogeneous catalytic decomposition of CHHP by the bis(tert-butyl)chromate has two serious defects. Firstly, during decomposing, the scale formation, mainly the chromium adipate, blocks equipments and pipelines. Disclosed by Rhodia, the phosphoric acid octyl ester is used as the scale inhibitor, which fails to completely solve the scale formation. The continuous production cycle only lasts for four months; washing and descaling after stalling the production device are executed three times per year. Secondly, the conversion rate is low, wherein the molar conversion rate is only around 92%; and around 5% of the CHHP still remains in the decomposed materials. The remaining CHHP is decomposed under the conditions of a high concentration of cyclohexanol and cyclohexanone, high acidity and a high temperature inside the cyclohexane recycling columns and the cyclohexanol and cyclohexanone product columns, so as to mainly produce acid compounds, like adipic acid, and ester compounds, mainly caprolactone; to speed up the condensation reaction of free radicals of the cyclohexanol and the cyclohexanone, and the esterification reaction of cyclohexanol; and to generate the high-boiling-point substances, and reduce the yield. Conventionally, the total molar yield of the domestic and foreign devices thereof is only around 80%.

The non-homogeneous catalytic decomposition by cobalt acetate in the alkaline aqueous solution of sodium hydroxide also has three defects. Firstly, the decomposition causes the big secondary reaction, and has a low molar yield of only 84%. Secondly, it is difficult to completely separate the cyclohexane oil phase containing cyclohexanol and cyclohexanone from the alkaline aqueous phase containing the alkaline waste. The oil phase always contains a certain amount of the waste alkaline aqueous phase, in such a manner that the scales of the waste alkaline are always formed in the rectification columns subsequently, which blocks the rectification columns and the reboilers thereof, and results in the continuous production cycle of only six months. Thirdly, the decomposition has a high alkali consumption and a large discharge capacity of alkali waste. A concentration of $OH^-$ ion in the alkali waste must be controlled around 1 mol/L. If the concentration of OH— ion is over 1 mol/L, difficulty of combustion of alkaline waste is increased; if below 1 mol/L, decomposition conversion rate is low, and part of the cyclohexyl hydrogen peroxide is decomposed continuously in an cyclohexane recycling column and a cyclohexane and cyclohexanone product column in the subsequent process, and caprolactone and organic acids are mainly generated, which decreases the total yield of the device and influences quality of cyclohexanone products. Currently, the conventional industrial devices adopting the process have the total molar yield of only about 80%.

Conventionally, the worldwide companies respectively adopt one of the above two manners to accomplish decomposing the CHHP at one step. The Chinese patents ZL9411039.9 and ZL98112730.4, filed by the inventor of this application, disclose the two-step decomposition art. At the first step thereof, the alkalinity is lowered; the recycling amount of the alkaline aqueous phase is increased; the static mixer is used. Industrial application results indicate that, the total molar yield of the device thereof really increases, but the separation of the cyclohexane oil phase from the waste alkaline aqueous phase becomes more difficult. The several sets of industrial production devices of the whole two-step decomposition art have a molar total yield of around 82%.

SUMMARY OF THE PRESENT INVENTION

An object of the present invention is to provide a process for preparing cyclohexanol and cyclohexanone by cyclohexane oxidation, which has a high total yield, a long continuous production cycle, a low consumption and cost.

In order to solve the technical problems mentioned above, the present invention provides a process for preparing cyclohexanol and cyclohexanone by cyclohexane oxidation, comprising steps of:

firstly processing uncatalyzed oxidation on cyclohexane by molecular oxygen, in such a manner that an oxidized mixture with cyclohexyl hydrogen peroxide serving as a primary product is generated;

then decomposing the cyclohexyl hydrogen peroxide to produce cyclohexanol and cyclohexanone; and then rectifying to obtain a cyclohexanol product and a cyclohexanone product;

wherein the step of decomposing the cyclohexyl hydrogen peroxide utilizes a three-step decomposition process combining a homogeneous catalytic decomposition process of bis(tert-butyl)chromate with a heterogeneous catalytic decomposition process of sodium hydroxide alkaline aqueous solution, comprising steps of:

(1) performing the homogeneous catalytic decomposition by utilizing the bis(tert-butyl)chromate as a catalyst;

(2) performing the heterogeneous catalytic decomposition in the sodium hydroxide alkaline aqueous solution under low alkalinity, wherein the low alkalinity means that a molar concentration of OH⁻ is at a range of 0.2~0.8 mol/L; and (3) performing the heterogeneous catalytic decomposition in the sodium hydroxide alkaline aqueous solution under high alkalinity, wherein the high alkalinity means that a molar concentration of OH⁻ is at a range of 0.9~2.2 mol/L.

Further, in the step (1) of decomposing the cyclohexyl hydrogen peroxide, while performing the homogeneous catalytic decomposition by utilizing the bis(tert-butyl)chromate as the catalyst, adding amount of the catalyst is equivalent to that a mass fraction of Chromium in cyclohexane oxidation liquid is at a range of 12±8 ppm, preferably 10 ppm.

Further, while performing the homogeneous catalytic decomposition by utilizing the bis(tert-butyl)chromate as the catalyst, a decomposition temperature is at a range of 60° C.~160° C., a decomposition pressure is at a range of 0.05 MPa~1.3 MPa, and a reactor residence time is at a range of 20~40 minutes, wherein the decomposition pressure is an absolute pressure.

Preferably, while performing the homogeneous catalytic decomposition by utilizing bis(tert-butyl)chromate as the catalyst, the decomposition temperature is at a range of 90±10° C., the decomposition pressure is at an atmospheric pressure, and the reactor residence time is at a range of 24~26 minutes, and preferably 25 minutes.

Further, performing the homogeneous catalytic decomposition by utilizing the bis(tert-butyl)chromate as the catalyst further comprises adding 1-hydroxy ethidene-1,1-diphosphonic acid (di)octyl ester for serving as a scale inhibitor, wherein adding amount of the 1-hydroxy ethidene-1,1-diphosphonic acid (di)octyl ester is equivalent to adding amount of Chromium which is an active component of the catalyst.

Further, in the step (2) of decomposing the cyclohexyl hydrogen peroxide under low alkalinity, a molarity of OH⁻ in sodium hydroxide aqueous solution is at a range of 0.5±0.2 mol/L, and a reactor residence time is at a range of 5~7 minutes, and preferably 6 minutes.

Further, in the step (3) for decomposing the cyclohexyl hydrogen peroxide under high alkalinity, the molarity of OH⁻ in sodium hydroxide aqueous solution is at a range of 1.5±0.5 mol/L, and a reactor residence time is at a range of 7~9 minutes, and preferably 8 minutes.

In the step (1) for decomposing the cyclohexyl hydrogen peroxide, the bis(tert-butyl)chromate is adopted as the catalyst for performing the homogeneous catalytic decomposition. Though a conversion rate of the decomposition is only at a range of 80~92%, a molar yield of the cyclohexanol and the cyclohexanone generated by the decomposition is capable of reaching 94%.

The process of the present invention adopts the 1-hydroxy ethidene-1,1-diphosphonic acid (di)octyl ester to replace phosphoric ester for serving as a scale inhibitor, which completely solves the problem of scale formation in cyclohexyl hydrogen peroxide homogeneous catalytic decomposition by bis(tert-butyl)chromate, in such a manner that a production cycle of the homogeneous catalytic decomposition reaches more than a year.

In the step (2) of performing the heterogeneous catalytic decomposition in the sodium hydroxide alkaline aqueous solution under low alkalinity, most of the cyclohexyl hydrogen peroxide which is not decomposed yet in the step (1) is processed with decomposition again to generate the cyclohexanol and the cyclohexanone, in such a manner that a conversion rate of the decomposition of the cyclohexyl hydrogen peroxide reaches 95%. Particularly, a concentration of sodium hydroxide of alkali waste separated in the step (2) of the decomposition is low. A molarity of OH⁻ in the alkali waste may be controlled to be at a range of 0.5±0.2 mol/L. Therefore, a portion of alkali water is discharged as alkali waste, so as to decrease discharge amount of the alkali waste, reduce a consumption of sodium hydroxide, and facilitate burning the alkali waste to reduce environmental pollution.

According to rules of Brown Lancaster, the reaction rate is directly proportional to the concentration of OH⁻, in the step (3) of performing the heterogeneous catalytic decomposition in the sodium hydroxide alkaline aqueous solution under the high alkalinity, the molarity of OH⁻ in the sodium hydroxide solution is controlled at a range of 1.5±0.5 mol/L, in such a manner that decomposition reaction is carried out fully and completely, decomposition conversion of the cyclohexyl hydrogen peroxide is completed, and the decomposition conversion is approximately 100%. Thus, the cyclohexyl hydrogen peroxide is prevented from decomposing into acids and esters in subsequent rectifying columns, and the cyclohexyl hydrogen peroxide is prevented from catalyzing a condensation reaction of free radicals of cyclohexanol and cyclohexanone in the rectifying columns with a high content of the cyclohexanol and the cyclohexanone, which affects a quality of cyclohexanone products and decreases a total yield of the device. In the step (3), the high alkalinity water phase of alkali is easy to perform settling separation from oil phase of cyclohexane, in such a manner that an amount of alkalinity water phase mixed in the oil phase of cyclohexane is decreased, which is in favor of prolonging a production cycle. Since the addition of the 1-hydroxy ethidene-1,1-diphosphonic acid (di)octyl ester completely solves the problems of blocking by scale formation, the liquid of cyclohexane oxidation may be performed with the cyclohexyl hydrogen peroxide homogeneous catalytic decomposition by the bis(tert-butyl)chromate after concentration and water washing, or otherwise be directly performed with the cyclohexyl hydrogen peroxide homogeneous catalytic decomposition by the bis(tert-butyl) chromate without the concentration and the water washing. During a process of the cyclohexyl hydrogen peroxide homogeneous catalytic decomposition by the bis(tert-butyl)chromate, a large amount of heat is released and water is produced. The heat may be removed by evaporating the cyclohexane and the water. The evaporated cyclohexane and the water are introduced into a rectifying and dehydrating column. A first part of the cyclohexane by distillation flows back, and a second part thereof returns back to a cyclohexane oxidation reactor. The water is settled and separated in a backflow slot, and then discharged into a wastewater recollection slot. Flow rate of the cyclohexane oxidation and decomposition liquid is decreased after the homogeneous decomposition, which is beneficial to separation of the oil phase and the alkaline water phase in the subsequent heterogeneous catalytic decomposition in the sodium hydroxide alkaline aqueous solution. In addition, during the process of the cyclohexyl hydrogen peroxide homogeneous catalytic decomposition by the bis(tert-butyl)chromate, an external circulating pump and a heater are provided to replace a stirrer in the conventional decomposition reaction, so as to increase evaporation amount of the cyclohexane and the water and stir by steam of the cyclohexane. Since the water is removed to a greatest extent by azeotropy, the impact of activity decline of the homogeneous catalyst caused by water is decreased, activity of the bis(tert-butyl)chromate is significantly increased, the decomposition conversion rate is improved, a ratio of cyclohexanone to cyclohexanol is significantly increased and scale formation rate is slowed sharply.

The process for preparing cyclohexanol and cyclohexanone by cyclohexane oxidation according to the present invention is capable of reaching a total molar yield of 85%.

These and other objectives, features, and advantages of the present invention will become apparent from the following detailed description, the accompanying drawings, and the appended claims.

BRIEF DESCRIPTION OF THE DRAWINGS

The FIGURE is a flow chart of a process for decomposing the cyclohexyl hydrogen peroxide according to a preferred embodiment of the present invention.

In the FIGURE, 1—pipeline I; 2—heat exchanger; 3—pipeline II; 4—pipeline III; 5—pipeline IV; 6—homogeneous catalytic decomposition reactor; 7—pipeline V; 8—pipeline VI; 9—pipeline VII; 10—pipeline VIII; 11—low-alkalinity heterogeneous catalytic decomposition reactor for step (2); 12—pipeline IX; 13—pipeline X; 14—pipeline XI; 15—high-alkalinity heterogeneous catalytic decomposition reactor for step (3); 16—pipeline XII; 17—pipeline XIII; 18—water washing device; 19—pipeline XIV; 20—pipeline XV.

DETAILED DESCRIPTION OF THE PREFERRED EMBODIMENT

Further description of the present invention is illustrated combining with preferred embodiments of the present invention.

The FIGURE is a flow chart of a process for decomposing the cyclohexyl hydrogen peroxide according to a preferred embodiment of the present invention. From a cyclohexane oxidation reactor, a cyclohexane oxidized mixture passes through a pipeline I 1, a heat exchanger 2 and a pipeline pipeline IV 5 and enters a homogeneous catalytic decomposition reactor 6;

wherein a weight flow rate of the cyclohexane oxidized mixture is 381.788 tons/hour; wherein the cyclohexane oxidized mixture passes through the heat exchanger 2 comprises components with weight percentages of: 95.27% cyclohexane, 3.4% cyclohexyl hydrogen peroxide, 0.37% cyclohexanol, 0.26% cyclohexanone, 0.28% acids, 0.28% esters, and 0.12% other components with a light weight;

wherein a temperature thereof drops from 166° C. to 114° C.;

wherein a weight ratio of bis(tert-butyl)chromate serving as a catalyst which is fed into the homogeneous catalytic decomposition reactor 6 from a pipeline VI 8 is 100 kg/h, a weight percentage of Chromium of the bis(tert-butyl)chromate is 3 wt %, in such a manner that a mass fraction of Chromium of the bis(tert-butyl)chromate serving as the catalyst in decomposition liquid is 10 ppm by weight;

then a scale inhibitor of 1-hydroxy ethidene-1,1-diphosphonic acid (di)octyl ester are fed into a pipeline VII 9 with a flow rate of 3 kg/h at a temperature range of 90±2° C., in such a manner that a step (1) of the homogeneous catalytic decomposition for decomposing the cyclohexyl hydrogen peroxide is performed under an atmospheric pressure, and a reactor residence time is 25 minutes. A conversion rate of decomposition of the cyclohexyl hydrogen peroxide is 90%, and a molar yield of the cyclohexanol and the cyclohexanone generated by the decomposition is 94%.

Decomposition heat and sensible heat of materials at an inlet causes a result that a large amount of cyclohexane is evaporated, which takes away water generated thereby, in such a manner that the cyclohexanol and the cyclohexanone in decomposition materials are concentrated.

In addition, a reboiler is provided in the homogeneous catalytic decomposition reactor 6, in such a manner that cyclohexane is steamed out at a rate of 100 tons/h in the homogeneous catalytic step. The steamed cyclohexane returns back to the cyclohexane oxidation reactor 6 through a pipeline V 7, so as to obtain a homogeneous catalytic decomposition reaction liquid around 281 tons/h, wherein components and mass percentages thereof are as follows: 94.15% cyclohexane, 0.46% cyclohexyl hydrogen peroxide, 1.49% cyclohexanol, 2.66% cyclohexanone, 0.46% acids, 0.59% esters, and 0.19% other components with a light weight.

Reaction mixtures after the homogeneous catalytic oxidation pass through a pipeline VIII 10 and enter a low-alkalinity heterogeneous catalytic decomposition reactor 11 for a step (2) of decomposing the cyclohexyl hydrogen peroxide. Since the reaction mixtures after the homogeneous catalytic oxidation contain 10 ppm of bis(tert-butyl)chromate serving as the catalyst already, addition of a transition metal ion catalyst is not required.

Low-alkalinity alkaline aqueous solution in the step (2) flows into a pipeline X 13, a molarity of NaOH in the alkaline aqueous solution is 1.5 mol/L, and a flow rate thereof is 18 tons/h. After mixed with circulating alkali, the molarity of NaOH drops to 0.6 mol/L. A heterogeneous catalytic decomposition under a low alkalinity in the step (2) adopts a piston flow reactor, i.e. a packed tower reactor. A residence time is 6 minutes. A conversion rate of the cyclohexyl hydrogen peroxide accounts for 5% of the total decomposition reaction. Main objects of the decomposition in the step (2) are to neutralize acids generated in the cyclohexane oxidation process and the decomposition process in the step (1), and to saponify ester contained in the materials.

After the low-alkalinity heterogeneous decomposition in the step (2), the materials are settled and separated, a first part of low concentration alkaline water phase in a low layer is circulated at 110 tons/h, and a rest part thereof is discharged from a pipeline IX 12 as alkali waste. A discharge rate of the alkali waste is 18 tons/h. Liquid of the alkali waste comprises 19 wt % by weight ratio of organic acids sodium, 0.5 wt % sodium hydroxide, 2.5 wt % sodium carbonate, and 78 wt % water.

In the step (2), an up layer of a separator after the low-alkalinity heterogeneous catalytic decomposition reactor 11 obtains an oil phase of organic decomposition reactants of the low-alkalinity heterogeneous catalytic decomposition reaction of the step (2), and components and mass percentages thereof are as follows: 94.74% cyclohexane, 0.23% cyclohexyl hydrogen peroxide, 1.85% cyclohexanol, 2.77% cyclohexanone, 0.01% acids, 0.2% esters, and 0.2% other components with a light weight.

The oil phase of organic decomposition reactants of the low-alkalinity heterogeneous catalytic decomposition reaction of the step (2) enters a high-alkalinity heterogeneous catalytic decomposition reactor 15 for a step (3) via a pipeline XI 14. A heterogeneous catalytic decomposition under a high alkalinity in the step (3) also adopts the piston flow reactor, i.e. the packed tower reactor. A residence time of materials is 8 minutes, and a weight flow rate is 278.5 t/h.

An alkaline solution with a mass concentration of 32% NaOH and a weight flow rate of 4400 Kg/h from a pipeline XII 16 and wash water with a weight flow rate of 10000 Kg/h from a pipeline 20 are mixed to enter the high-alkalinity heterogeneous catalytic decomposition reactor 15 for the step (3) for processing the high-alkalinity heterogeneous catalytic decomposition therein.

Since the scale inhibitor 1-hydroxy ethidene-1,1-diphosphonic acid (di)octyl ester is capable of dissolving a part of the catalyst of the bis(tert-butyl)chromate into the oil phase, addition of the catalyst of the bis(tert-butyl)chromate in the step (3) for decomposition is not required.

In decomposition liquid of the step (3), a decomposition conversion of the cyclohexyl hydrogen peroxide is complete, and the esters are saponified completely. In the step (3), the decomposition liquid is separated in a settling separator. A low layer is a alkaline water phase containing 1.5 mol/L of $OH^-$, wherein a first part thereof is circulated at a weight flow rate of 18 tons/h, a second part thereof passes through the pipeline X 13 and returns back to the low-alkalinity heterogeneous catalytic decomposition reactor 11 for the step (2).

An organic oil phase in an up layer of the high-alkalinity heterogeneous catalytic decomposition reactor 15 for the step (3) enters a water washing device 18 via a pipeline XIII 17. Fresh wash water passes through a pipeline XIV 19 and enters the pipeline XIII 17 to be mixed with the organic oil phase on the up layer of the high-alkalinity heterogeneous catalytic decomposition reactor 15 for the step (3), and then enters the water washing device 18 to wash off a small amount of alkaline liquid contained in the organic oil. A lower layer of water in a water washing separator of the water washing device 18 is discharged from a pipeline XV 20 at a weight flow rate of 10 tons/h for diluting fresh alkaline liquid.

An upper layer of organic oil in the water washing separator returns back to a heat exchanger 2 via the pipeline II 3 to perform heat exchanging with the cyclohexane oxidation liquid. A flow rate of the organic oil phase is 278.4 t/h, components and mass percentages thereof are as follows: 94.97% cyclohexane, <0.01% cyclohexyl hydrogen peroxide, 1.97% cyclohexanol, 2.86% cyclohexanone, 0% acids, <0.01% esters, and 0.2% other components with a light weight.

After the high-alkalinity heterogeneous decomposition in the step (3) and the heat exchanging in the heat exchanger 2, the organic oil phase decomposition liquid is sent to a set of cyclohexane columns via a pipeline III 4 to steam out cyclohexane. Oxidized decomposition products pass through a light column, a cyclohexanone column and a cyclohexanol column and a dehydrogenation system for processing. Finally, a cyclohexanone product with a weight flow rate of 13175 Kg/h is obtained, which contains 99.95% of cyclohexanone by weight. Furthermore, heavy-component X oil with a weight flow rate of 400 Kg/h and light-component light oil with a weight flow rate of 160 Kg/h are obtained.

In the preferred embodiment of the present invention, a total yield from benzene hydrogenation for producing cyclohexane to cyclohexane oxidation for producing cyclohexanone is 85%, i.e., a total consumption of the device is (13.192 tons/h of cyclohexane)/(13175 Kg/h of cyclohexanone)=1001.3 Kg cyclohexane/ton cyclohexanone=930 Kg benzene/ton cyclohexanone. Consumption of alkali 4400/13.175=334 Kg (32 wt %) NaOH/ton cyclohexanone.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A process for preparing cyclohexanol and cyclohexanone by cyclohexane oxidation, comprising steps of:
   firstly processing uncatalyzed oxidation on cyclohexane by molecular oxygen, in such a manner that an oxidized mixture with cyclohexyl hydrogen peroxide serving as a primary product is generated;
   then decomposing the cyclohexyl hydrogen peroxide to produce cyclohexanol and cyclohexanone; and
   then rectifying to obtain a cyclohexanol product and a cyclohexanone product;
   wherein the step of decomposing the cyclohexyl hydrogen peroxide utilizes a three-step decomposition process combining a homogeneous catalytic decomposition process of bis(tert-butyl) chromate with a heterogeneous catalytic decomposition process of sodium hydroxide alkaline aqueous solution, comprising steps of:
   (1) performing the homogeneous catalytic decomposition by utilizing the bis(tert-butyl) chromate as a catalyst, adding 1-hydroxy ethidene-1,1-diphosphonic acid (di) octyl ester for serving as a scale inhibitor, wherein adding amount of the 1-hydroxy ethidene-1,1-diphosphonic acid (di)octyl ester is equivalent to adding amount of Chromium which is an active component of the catalyst; wherein the decomposition temperature is at a range of 90±10° C., the decomposition pressure is at an atmospheric pressure, and the reactor residence time is at a range of 24~26 minutes;
   (2) performing the heterogeneous catalytic decomposition in the sodium hydroxide alkaline aqueous solution under low alkalinity, wherein the low alkalinity means that a molar concentration of $OH^-$ is at a range of 0.2~0.8 mol/L; and
   (3) performing the heterogeneous catalytic decomposition in the sodium hydroxide alkaline aqueous solution under high alkalinity, wherein the high alkalinity means that a molar concentration of $OH^-$ is at a range of 0.9~2.2 mol/L.

2. The process for preparing cyclohexanol and cyclohexanone by cyclohexane oxidation, as recited in claim 1, wherein in the step (1) of decomposing the cyclohexyl hydrogen peroxide, while performing the homogeneous catalytic decomposition by utilizing the bis(tert-butyl) chromate as the catalyst, adding amount of the catalyst is equivalent to that a mass fraction of Chromium in cyclohexane oxidation liquid is at a range of 12±8 ppm.

3. The process for preparing cyclohexanol and cyclohexanone by cyclohexane oxidation, as recited in claim 1, wherein the reactor residence time is 25 minutes.

4. The process for preparing cyclohexanol and cyclohexanone by cyclohexane oxidation, as recited in claim 1, wherein in the step (2) for decomposing the cyclohexyl hydrogen peroxide under low alkalinity, a molarity of Off in sodium hydroxide aqueous solution is at a range of 0.5±0.2 mol/L, and a reactor residence time is at a range of 5~7 minutes.

5. The process for preparing cyclohexanol and cyclohexanone by cyclohexane oxidation, as recited in claim 2, wherein in the step (2) for decomposing the cyclohexyl hydrogen peroxide under low alkalinity, a molarity of $OH^-$ in sodium hydroxide aqueous solution is at a range of 0.5±0.2 mol/L, and a reactor residence time is at a range of 5~7 minutes.

6. The process for preparing cyclohexanol and cyclohexanone by cyclohexane oxidation, as recited in claim 3, wherein in the step (2) for decomposing the cyclohexyl hydrogen peroxide under low alkalinity, a molarity of $OH^-$ in sodium hydroxide aqueous solution is at a range of 0.5±0.2 mol/L, and a reactor residence time is at a range of 5-7 minutes.

7. The process for preparing cyclohexanol and cyclohexanone by cyclohexane oxidation, as recited in claim 4, wherein the reactor residence time is 6 minutes.

8. The process for preparing cyclohexanol and cyclohexanone by cyclohexane oxidation, as recited in claim 5, wherein the reactor residence time is 6 minutes.

9. The process for preparing cyclohexanol and cyclohexanone by cyclohexane oxidation, as recited in claim 6, wherein the reactor residence time is 6 minutes.

10. The process for preparing cyclohexanol and cyclohexanone by cyclohexane oxidation, as recited in claim 1, wherein in the step (3) for decomposing the cyclohexyl hydrogen peroxide under high alkalinity, a molarity of $OH^-$ in sodium hydroxide aqueous solution is at a range of 1.5±0.5 mol/L, and a reactor residence time is at a range of 7-9 minutes.

11. The process for preparing cyclohexanol and cyclohexanone by cyclohexane oxidation, as recited in claim 2, wherein in the step (3) for decomposing the cyclohexyl hydrogen peroxide under high alkalinity, a molarity of $OH^-$ in sodium hydroxide aqueous solution is at a range of 1.5±0.5 mol/L, and a reactor residence time is at a range of 7-9 minutes.

12. The process for preparing cyclohexanol and cyclohexanone by cyclohexane oxidation, as recited in claim 3, wherein in the step (3) for decomposing the cyclohexyl hydrogen peroxide under high alkalinity, a molarity of $OH^-$ in sodium hydroxide aqueous solution is at a range of 1.5±0.5 mol/L, and a reactor residence time is at a range of 7~9 minutes.

13. The process for preparing cyclohexanol and cyclohexanone by cyclohexane oxidation, as recited in claim 4, wherein in the step (3) for decomposing the cyclohexyl hydrogen peroxide under high alkalinity, a molarity of $OH^-$ in sodium hydroxide aqueous solution is at a range of 1.5±0.5 mol/L, and a reactor residence time is at a range of 7~9 minutes.

14. The process for preparing cyclohexanol and cyclohexanone by cyclohexane oxidation, as recited in claim 5, wherein in the step (3) for decomposing the cyclohexyl hydrogen peroxide under high alkalinity, a molarity of $OH^-$ in sodium hydroxide aqueous solution is at a range of 1.5±0.5 mol/L, and a reactor residence time is at a range of 7~9 minutes.

15. The process for preparing cyclohexanol and cyclohexanone by cyclohexane oxidation, as recited in claim 6, wherein in the step (3) for decomposing the cyclohexyl hydrogen peroxide under high alkalinity, a molarity of $OH^-$ in sodium hydroxide aqueous solution is at a range of 1.5±0.5 mol/L, and a reactor residence time is at a range of 7~9 minutes.

16. The process for preparing cyclohexanol and cyclohexanone by cyclohexane oxidation, as recited in claim 10, wherein the reactor residence time is 8 minutes.

17. The process for preparing cyclohexanol and cyclohexanone by cyclohexane oxidation, as recited in claim 11, wherein the reactor residence time is 8 minutes.

18. The process for preparing cyclohexanol and cyclohexanone by cyclohexane oxidation, as recited in claim 12, wherein the reactor residence time is 8 minutes.

\* \* \* \* \*